United States Patent [19]

Rusin et al.

[11] Patent Number: 5,413,624
[45] Date of Patent: May 9, 1995

[54] ENHANCEMENT OF BIOLEACH SYSTEMS USING NUTRIENT ADDITIVES

[75] Inventors: Patricia A. Rusin; James E. Sharp, both of Tucson, Ariz.

[73] Assignee: MBX Systems, Inc., Tucson, Ariz.

[21] Appl. No.: 194,676

[22] Filed: Feb. 14, 1994

Related U.S. Application Data

[63] Continuation-in-part of Ser. No. 127,394, Sep. 27, 1993, which is a continuation-in-part of Ser. No. 23,990, Feb. 26, 1993, Pat. No. 5,248,329, which is a continuation-in-part of Ser. No. 828,056, Jan. 30, 1992, Pat. No. 5,221,327, which is a continuation-in-part of Ser. No. 682,491, Apr. 9, 1991, abandoned, which is a continuation-in-part of Ser. No. 660,312, Feb. 22, 1991, abandoned.

[51] Int. Cl.$^6$ .............................................. C22B 11/04
[52] U.S. Cl. ................................ 75/711; 423/DIG. 17
[58] Field of Search .................. 75/711; 423/DIG. 17

[56] References Cited

U.S. PATENT DOCUMENTS

| | | | |
|---|---|---|---|
| 3,154,403 | 10/1964 | Stickley | 75/321 |
| 4,402,736 | 9/1983 | Graham | 75/321 |
| 4,571,387 | 2/1986 | Bruynesteyn | 423/DIG. 17 |
| 4,732,681 | 3/1988 | Galun | 423/DIG. 17 |
| 4,822,413 | 4/1989 | Pooley | 423/DIG. 17 |
| 5,209,851 | 5/1993 | Hume | 423/DIG. 17 |

OTHER PUBLICATIONS

Colmer, A. R., M. E. Hinkle (1947) "The Role of Microorganisms in Acid Mine Drainage: A Preliminary Report" Science 106:253–256.

Huber, H., K. O. Stetter (1989) "*Thiobacillus prosperus* sp. nov., represents a new group of halotolerant metal-mobilizing bacteria isolated from a marine geothermal field": Archives of Microbiology 151:479–485.

Huber, H., K. O. Stetter (1990) "Thiobacillus cuprinus sp. nov., a Novel Facultatively Organotrophic Metal-Mobilizing Bacterium" Applied and Environmental Microbiology 56(2):315–322.

Manchee, R. (1979) "Microbial Mining" TIBS, Apr. 1979:77–80.

Puhakka, J., O. H. Tuovinen (1987) "Effect of organic compounds on the microbiological leaching of a complex sulphide ore material" MIRCEN Journal of Applied Microbiology and Biotechnology 3:429–436.

Stevens, C. J. et al. (1986) "Acetylene Reduction (Nitrogen Fixation) by *Thiobacillus ferrooxidans*" Biotechnology and Applied Biochemistry 8:351–359.

Torma, A. E. et al. (1976) "Effects of Surface Active Agents on the Oxidation of Chalcopyrite by *Thiobacillus ferrooxidans*" Hydrometallurgy 1:301–309.

Tuttle, J. H., P. R. Dugan (1976) "Inhibition of growth, iron, and sulfur oxidation in *Thiobacillus ferrooxidans* by simple organic compounds" Canadian Journal of Microbiology 22:719–730.

*Primary Examiner*—Peter D. Rosenberg
*Attorney, Agent, or Firm*—Saliwanchik & Saliwanchik

[57] ABSTRACT

Materials and methods for the enhancement of the bi-ooxidative acid leaching of heavy metals from sulfide ore are disclosed and claimed. The enhancement of bioleach solutions with a nutrient supplement selective for a particular sulfide oxidizing strain of bacteria significantly increases copper solubilization of chalcopyrite ore. Likewise, copper solubilization is enhanced by enriching bioleach solutions with a non-selective growth mediums.

11 Claims, 5 Drawing Sheets

FIGURE 5

ENHANCEMENT OF BIOLEACH SYSTEMS USING NUTRIENT ADDITIVES

CROSS-REFERENCE TO A RELATED APPLICATION

This application is a continuation-in-part of application Ser. No. 08/127,394, filed on Sep. 27, 1993; which is a continuation-in-part of application Ser. No. 08/023,990, filed Feb. 26, 1993, now U.S. Pat. No. 5,248,329; which a continuation-in-part of application Serial No. 07/828,056, filed January 30, 1992, now U.S. Pat. No. 5,221,327; which is a continuation-in-part of application Ser. No. 07/682,491, filed on Apr. 9, 1991, now abandoned, which was a continuation-in-part of application Ser. No. 07/660,312, filed Feb. 22, 1991, now abandoned.

BACKGROUND OF THE INVENTION

The ancient Romans are thought to have been the first to recover metal using a biological process. It is believed that they took advantage of natural sites to recover copper sulfate resulting from the microbial biooxidative acid leaching of sulfide ore. Details of the copper recovery process were not documented until 1670 at Rio Tinto in Spain. The methods documented in 1670 are still used today. One organism instrumental in the modern use of this biological recovery process is *Thiobacillus ferrooxidans*, which was isolated in 1947 from an abandoned coal mine in West Virginia (Colmer [1947]). This organism's activity is normally limited by the amount of substrate exposed to the atmosphere where the necessary oxygen is present to carry out the oxidation of the metal sulfide.

Although deposits of high grade ore are frequently most efficiently extracted by smelting, it has been found that low grade inherent deposits of sulfide ore can be extracted by heap leaching which utilizes the biooxidation processes (Manchee [1979]). In this process, roughly fist-sized lumps of ore are piled upon a surface that is impervious to liquids. Water is applied to the top of the heap by a sprinkler system to provide moisture for the natural flora and to create a constant flow of fluid throughout the pile. Within the heap, two methods of leaching occur. The first occurs at the surface of the pile where the natural flora, in the presence of oxygen, attack iron pyrites producing ferric sulfate and sulfuric acid. The bacteria likewise act upon other mineral sulfides to dissolve other metallic minerals as well. In the center of the heap, out of the presence of oxygen, a second leaching process occurs. This indirect leaching is a purely chemical process by which the highly oxidizing acidic ferric sulfate produced by the bacterial leaching process at the surface of the pile reacts with mineral sulfides and oxides. Effluent running from the heap containing the products of these two leaching processes can be collected and treated to recover purified metal ore.

Normally the heap need not be inoculated with extraneous bacteria but rather the heap's natural flora is relied upon for the leaching process. Similar biooxidative processes are exploited for in situ leaching situations. Enargrite, $Cu_3(As,Sb)S_4$; Chalcopyrite, $CuFeS_2$; Bornite, $Cu_5FeS_4$; Covellite, $CuS$; Chalcocite, $Cu_2S$; Tetrahedrite, $Cu_8Sb_2S_7$; and Chalcomenite, $CuSeO_3.2-H_2O$ are examples of the copper ores which are amenable to this biooxidative process. Other metals that can be recovered by the process of sulfide biooxidation include iron, molybdenum, nickel, lead, arsenic, antimony, tin, uranium, vanadium, gold, and zinc.

In the case of copper recovery, copper sulfide breaks down more slowly than copper oxide because sulfide minerals are composed of reduced sulfur and iron that must be oxidized in order for dissolution to occur. Bacterial oxidation is important to the dissolution of copper sulfide minerals, particularly chalcopyrite, and to a lesser extent, chalcocite.

Several kinds of bacteria have been described that oxidize reduced forms of iron and/or sulfur including *Thiobacillus ferrooxidans*, *T. thiooxidans*, *Leptospirillum ferrooxidans*, Sulfolobus, Acidianus, Sulfobacillus, Strain ALV, Strain LM2, and others. New strains of mineral-oxidizing bacteria have more recently been described by Huber and Stetter (1989, 1990) called *T. cuprinus* and *T. prosperus*.

While *T. ferrooxidans* has received the most attention, as mentioned above, many other microbes are present in heaps and dumps that can contribute to the extraction of copper. Most of these sulfide/iron-oxidizing bacteria are capable of using carbon dioxide to satisfy their carbon needs. Many organic compounds inhibit *T. ferrooxidans* (Torma et al. [1976]; Tuttle and Dugan [1976]; and Puhakka and Tuovinan [1987]). *T. cuprinus*, however can use certain forms of organic carbon. The limiting nutrients for most bacteria found in the ore containing environment are nitrogen and phosphorus. The most preferred form of nitrogen for these organisms is ammonium; phosphate serves as a source of phosphorus. These nutrients must be solubilized before the bacteria can use them. Phosphate requirements may also be satisfied if minerals such as apatite are present and solubilized. Some strains of *T. ferrooxidans* are able to use atmospheric nitrogen if ammonium nitrogen is not available (Stevens et al. [1986]).

BRIEF SUMMARY OF THE INVENTION

The subject invention relates generally to a microbial bioremediation method for recovering heavy metals from ore. In a preferred embodiment, the subject invention relates to an improved method for the microbial biooxidative acid leaching of heavy metals from sulfide ore. The method comprises contacting said ore with novel nutrient supplements. The supplements enhance the growth of the natural flora on the ore. The bacteria of the natural flora solubilize the ore into a form that is more amenable to refinement.

In a specific embodiment exemplified herein, a nutrient medium is sprayed onto a mineral ore leach pile to recover copper from the ore. In preferred embodiments the nutrient medium can comprise extracts prepared from corn or potatoes as described herein.

DETAILED DESCRIPTION OF THE INVENTION

The subject invention concerns new materials and methods for the efficient extraction of useful metals for ores, including low grade ores. Because the process of the subject invention reduces or eliminates the use of hazardous chemicals, it is advantageous from an environmental standpoint. The process of the subject invention utilizes bioremediation properties of microbes to liberate desired metals from ores. In a preferred embodiment the process of the subject invention utilizes microbes which exist naturally in the ore which is to be processed. The biooxidative properties of these indigenous microbes is activated, enhanced, or augmented by the administration of aqueous nutrient solutions. Specifically exemplified herein are nutrient solutions which are derived from potato and corn sources. These nutrient solutions are referred to herein as Potato Extract Growth Medium (PEGM) and Corn Extract Growth Medium (CGM).

As described herein, the nutrient mediums of the subject invention are administered directly to ores, such as in leach heaps, and advantageously and surprisingly, these nutrient sources are able to markedly increase the extraction of useful metals from even low grade ores. This enhanced extraction efficiency is observed even without seeding the ore with desired microbes and without adding agents which help to select for specific microbes.

The subject invention is specifically exemplified herein with reference to the extraction of copper from sulfides in ore. In a preferred embodiment PEGM or CGM is added to copper sulfite ore pries using sprinklers, hoses, or the like. The rate of delivery will depend on the particular setting but can be in the range of about 100 to about 500 gal/day and, preferably, about 250 gal/day. The concentration of the nutrient solution can be about 5 to about 25% in water and is preferably about 10%. The addition of PEGM or CGM was discovered to result in the recovery of useful quantities of copper from the ore. In further embodiments of the invention, the natural flora can be manipulated by either adding additional microbes or by adding agents which will preferentially select for certain desired microbes.

Although seeding of heap pries with microbes is not necessary when using the procedure of the subject invention, if addition of microbes is desired then a variety of microbes can be used which are known and available to those skilled in the art. In addition to the various microbes described herein, additional microbes are described in, for example, U.S. Pat. No. 5,055,130 (*Bacillus polymyxa*) and U.S. Pat. No. 5,221,327 (Bacillus MBX 69 and mutants thereof). These patents are incorporated herein by reference.

In conventional copper mining operations, ore is first treated with an "On" solution. This solution extracts copper sulfite from the sulfides in ore. The resulting copper sulfate is sent to a solvent extraction plant where purified copper is stripped from the solution.

Materials and Methods

Variables were evaluated in the composition of the solutions for effects on copper solubilization of copper sulfide ore. Variables evaluated included: The addition of nutrient supplements to the solution, seeding the solution with the microbes *T. ferrooxidans* or *T. cuprinus*, and comparisons of growth media. Unmodified On solutions were used as a baseline control. Nutrient supplements evaluated included supplements favoring the growth of either *T. ferrooxidans* (designated TFN), or supplements favoring the growth of *T. cuprinus* (designated TCN). TFN and TCN, or variations thereof, are known and available to the public from, for example, ATCC. A nutrient supplement designated as PEGM (U.S. Pat. No. 5,248,329) was also tested at a final concentration of 10%. Additives to the On solution that match concentrations found in growth Medium 64, described by ATCC (1989), or growth Medium 30 were evaluated.

As used herein, PEGM refers to the composition which is obtained when raw potatoes are cut up and heated in the presence of water. Typically, the potatoes will be boiled in water for about 15 to about 60 minutes, preferably about 30 minutes. The amount of water used can vary and the medium obtained can be diluted. The relative percentages of non-water constituents, however, will remain approximately the same. The composition of a PEGM is provided in Table 1.

TABLE 1

| Composition of a PEGM | | |
|---|---|---|
| | Fresh[1] | Range[1] |
| Water | 77 | 69–85 |
| Ash | 1 | 0.08–1.2 |
| Protein | 2.5 | 2.0–3.0 |
| Fat | 0.1 | 0.08–0.13 |
| Fiber | 0.4 | 0.2–0.6 |
| Carbohydrate | 20.3 | 18–22 |
| Vitamin A | trace | trace |
| Ascorbic Acid | 200 mg/kg (0.02%) | 0.01–0.03 |
| Niacin | 15 mg/kg (0.0015%) | 0.0012–0.0010 |
| Thiamine | 1.0 mg/kg (0.0001%) | 0.00005–0.0003 |
| Riboflavin | 0.4 mg/kg (0.00004%) | 0.00002–0.00006 |
| Iron | 0.001 | 0.01–0.0005 |
| Phosphorus | 0.05 | 0.02–0.08 |
| Potassium | 0.41 | 0.2–0.6 |
| Sodium | 0.02 | 0.01–0.03 |
| Chloride | 0.07 | 0.05–0.1 |
| Copper | 4.1 mg/kg (0.00041%) | 0.0002–0.0006 |
| Magnesium | 0.03 | 0.02–0.04 |
| Manganese | 9.6 mg/kg (0.00096%) | 0.0007–0.002 |
| Calcium | 0.01 | 0.05–0.02 |
| Sulfur | 0.02 | 0.01–0.03 |

[1]Concentrations are in percent unless otherwise noted.

Corn Extract Growth Medium, or CGM, may also be used according to the subject invention. As used herein CGM refers to the extract obtained when corn cobs are chopped and boiled in water. Typically, the corn cobs are chopped into pieces of a couple to several inches, and boiled in water for about 15 to about 60 minutes, preferably about 30 minutes. The amount of water used can be varied and the medium obtained can be diluted. The relative percentages of non-water constituents, however, will remain approximately the same. The composition of a CGM is provided in Table 2.

TABLE 2

| Composition of a CGM | |
|---|---|
| Composition (%) | Range (%) |
| Ash 1.6 | 1.46–1.74 |

TABLE 2-continued

| Composition of a CGM | | |
|---|---|---|
| | Composition (%) | Range (%) |
| Fiber | 2.7 | 2.4–3.0 |
| Protein | 12.1 | 10.9–13.3 |
| Fat | 5.4 | 4.9–5.9 |
| Carbohydrate | 84.4 | 76.0–92.8 |
| Vitamin A | 310.0 IU | 282–338 |
| Ascorbic acid | 0.02 | 0.01–0.03 |
| Niacin | 0.03 | 0.01–0.05 |
| Thiamine | 0.0003 | 0.00027–0.00033 |
| Riboflavin | 0.0013 | 0.0012–0.0014 |
| Iron | 0.001 | 0.0009–0.0013 |
| Magnesium | 0.13 | 0.116–0.144 |
| Phosphorous | 0.34 | 0.2–0.4 |
| Sulfur | 0.1 | 0.08–0.13 |
| Potassium | 0.4 | 0.2–0.6 |
| Calcium | 0.02 | 0.01–0.03 |
| Choline | 0.6 | 0.5–0.7 |
| Pantothenic acid | 0.007 | 0.0062–0.0078 |
| Pyridoxine | 0.009 | 0.0079–0.01 |
| Arginine | 0.6 | 0.5–0.7 |
| Cystine | 0.1 | 0.07–0.2 |
| Glycine | 0.5 | 0.4–0.6 |
| Histidine | 0.2 | 0.1–0.3 |
| Isoleucine | 0.5 | 0.45–0.55 |
| Leucine | 1.3 | 1.17–1.43 |
| Lysine | 0.2 | 0.15–0.25 |
| Methionine | 0.2 | 0.1–0.3 |
| Phenylalanine | 0.6 | 0.5–0.7 |
| Threonine | 0.5 | 0.4–0.6 |
| Tryptophan | 0.1 | 0.06–0.22 |
| Valine | 0.5 | 0.46–0.56 |

The following constituents of the PEGM and the CGM are the most critical for support of bacterial growth and to aid in the claimed processes: protein, carbohydrates, sulfur, niacin, thiamine, riboflavin, phosphorus, potassium and magnesium.

Thus, the PEGM used according to the subject invention can comprise the following ingredients:

TABLE 3

| Ingredient | Concentration Range (%) |
|---|---|
| Protein | 2.0–3.0 |
| Carbohydrate | 18–22 |
| Niacin | 0.0012–0.0010 |
| Thiamine | 0.00005–0.00003 |
| Riboflavin | 0.00002–0.00006 |
| Phosphorous | 0.02–0.08 |
| Potassium | 0.2–0.6 |
| Magnesium | 0.02–0.04 |
| Sulfur | 0.01–0.03 |

In a preferred embodiment the approximate concentrations of ingredients in the PEGM can be:

TABLE 4

| Ingredient | Approximate Concentration (%) |
|---|---|
| Protein | 2.5 |
| Carbohydrate | 20.3 |
| Niacin | 0.0015 |
| Thiamine | 0.0001 |
| Riboflavin | 0.00004 |
| Phosphorous | 0.05 |
| Potassium | 0.41 |
| Magnesium | 0.03 |
| Sulfur | 0.2 |

Similarly, the CGM of the subject invention can comprise the following ingredients:

TABLE 5

| Ingredient | Range of Concentration (%) |
|---|---|
| Protein | 10.9–13.3 |

TABLE 5-continued

| Ingredient | Range of Concentration (%) |
|---|---|
| Carbohydrate | 76.0–92.8 |
| Niacin | 0.01–0.05 |
| Thiamine | 0.00027–0.00033 |
| Riboflavin | 0.0012–0.0014 |
| Phosphorous | 0.2–0.4 |
| Sulfur | 0.08–0.13 |
| Potassium | 0.2–0.6 |
| Magnesium | 0.116–0.144 |

In a preferred embodiment the approximate concentrations of the ingredients in the CGM can be:

TABLE 6

| Ingredient | Approximate Concentration (%) |
|---|---|
| Protein | 12.1 |
| Carbohydrate | 84.4 |
| Niacin | 0.03 |
| Thiamine | 0.0003 |
| Riboflavin | 0.0013 |
| Phosphorous | 0.34 |
| Sulfur | 0.1 |
| Potassium | 0.4 |
| Magnesium | 0.13 |

Medium 30 of the subject invention, contains the following per liter of distilled water:

TABLE 7

| Ingredient | Amount |
|---|---|
| $NH_4Cl$ | 1.25 g |
| KCl | 0.33 g |
| $K_2HPO_4$ | 0.14 g |
| $MgSO_4.7H_2O$ | 3.45 g |
| $MgCl_2.6H_2O$ | 2.75 g |
| $CaCl_2.2H_2O$ | 0.14 g |
| $KH_2PO_4$ | 0.14 g |
| NaCl | 0.50 g |
| $NiCl_2.6H_2O$ | 0.002 g |
| yeast extract | 0.50 g |
| trace element solution* | 10 ml |

*Balch et al. (1979)

A 0.1% sodium solution was added to some control shake flasks to sterilize the On solution and ore. These sterile flasks were included to determine whether bacterial activity was actually contributing to the copper extraction from sulfide ore. In some cases, ore was sterilized by autoclaving (121° C., 15 min, 15 psi).

A 10% pulp density and minus200 mesh ore were used in all cases. Shake flasks were rotated at ≈130 rpm. Solution pH, Eh, solubilized copper, ferrous iron, and total iron were determined weekly. Soluble copper and iron were determined by atomic absorption (AA). Ferrous iron was determined by the Ferrozine method as described by Gibbs (1976). Midway in the test period, leach solutions were revitalized by replacing half the volume with fresh solution. Most Probable Number (MPN) enumeration of Thiobacillus sp. was determined at intervals using standard methods (APHA, 1989). Solution pH was adjusted with $H_2SO_4$ or NaOH at each sampling period. For *T. cuprinus*, the target pH range was 2.5 to 4.0. For *T. ferrooxidans*, the target range was pH 1.6 to 2.4.

At the end of each test period, residual solids (tails) were washed three times with distilled water, dried, and weighed. Shake flask tails and heads were digested for AA analyses using aqua regia and perchloric acid. A metallurgical balance was calculated in each case.

All treatments were tested in duplicate. Statistical analyses were performed using one-way analysis of variance.

Following are examples which illustrate procedures, including the best mode, for practicing the invention. These examples should not be constructed as limiting. All percentages are by weight and all solvent mixture proportions are by volume unless otherwise noted.

EXAMPLE 1

Effects of Variations in the Leach Solutions on the Copper Extraction of Sample Ore A Copper sulfide ore sample A had a head assay of 0.22% copper of which 22.7% was acid soluble. According to a mineralogical analysis, most of the copper was in the form of chalcopyrite having a minor quantity of digenite. The ore also contained 2.65% iron and 1.6% sulfur of which 97% was in the sulfide form.

Table 8 shows the effect that variations in the leach solutions have on copper extraction. As shown in Table 8, sterilization of the On solution and ore by the addition of 0.10% sodium benzoate to kill all native flora resulted in a significant decrease in copper extraction ($p = 0.011$). The results of these studies attest to the importance of microorganisms for the leaching of such refractory sulfide compounds.

TABLE 8

Metallurgical balances for Ore Sample A[1]

| Leach Solution | Amount of Copper in Milligrams | | | |
|---|---|---|---|---|
| | Cu in Solution | Leached Tails | Calc. Head | % Cu Extr. |
| Sterile On Soln. + Ore | 6.05 | 15.8 | 21.8 | 27.6 |
| On Soln. | 6.9 | 13.9 | 20.8 | 33.0 |
| On soln. + TFN | 6.3 | 12.1 | 18.5 | 34.3 |
| On soln. + TCN | 7.9 | 12.8 | 20.7 | 38.1 |
| On soln. + TCN + T. cuprinus | 7.8 | 12.5 | 20.3 | 38.5 |
| On soln. + PEGM | 10.0 | 11.7 | 21.7 | 46.2 |
| Medium 64 | 7.7 | 11.0 | 18.7 | 41.1 |
| Medium 64− | 8.3 | 12.2 | 20.6 | 40.5 |
| Medium 30 | 7.6 | 12.2 | 19.7 | 38.3 |
| Medium 64− + T. ferrooxidans | 8.4 | 11.7 | 20.1 | 41.7 |
| Medium 30 + T. cuprinus[2] | 7.2 | 14.0 | 21.2 | 33.9 |

[1]Head assay in all cases = 22.0 mg.
[2]Ore was sterilized by autoclave.

Figure 1:
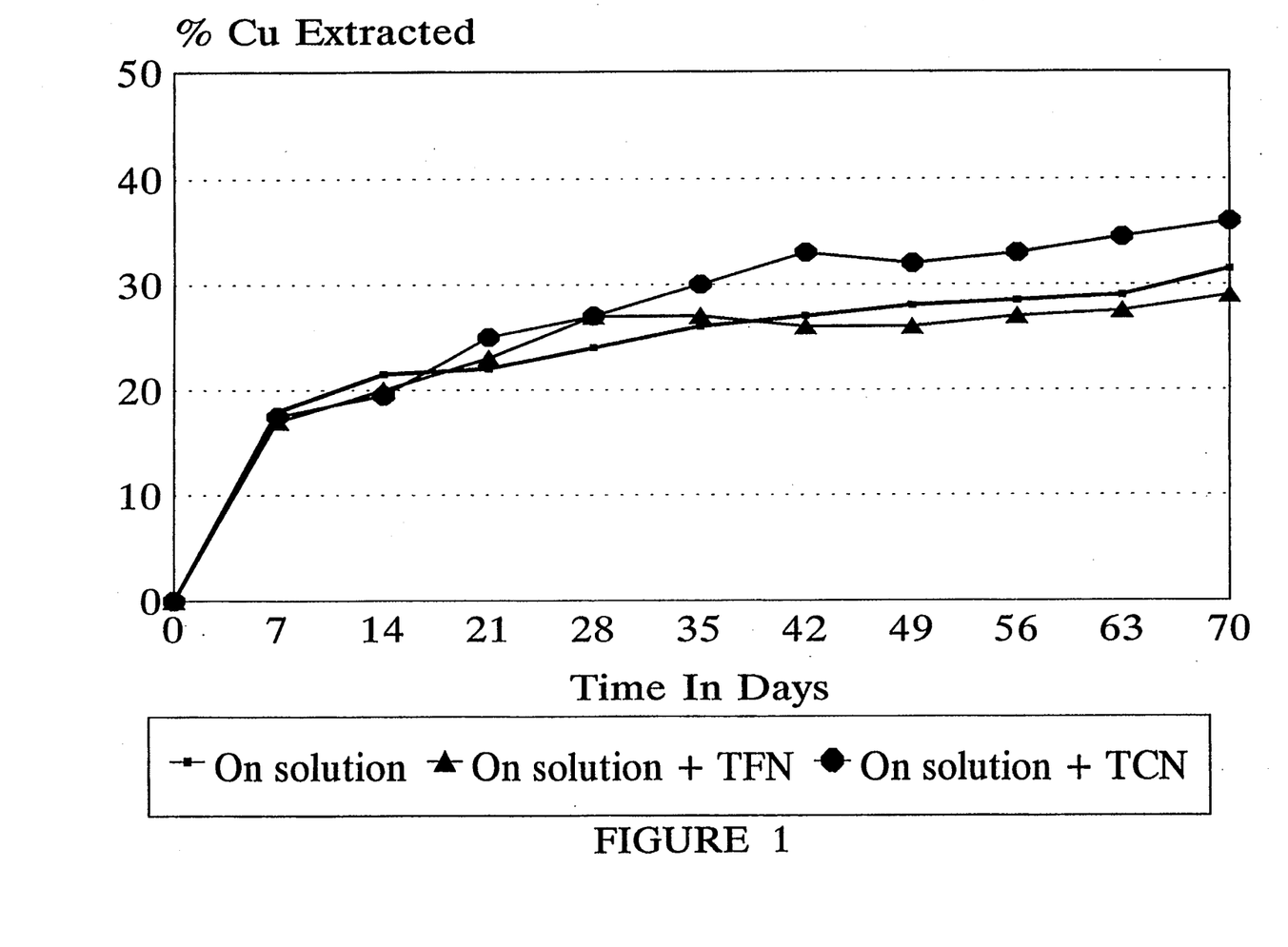
FIG. 1. Rates of copper extraction from sulfide ore using unmodified On solution and On solution supplemented with nutrients designated TFN and TCN, respectively.

FIG. 1 shows rates of copper extraction achieved using unmodified On solution, On solution amended with 1.9% TFN nutrients, and On solution amended with 0.16% TCN nutrients. No significant increase in copper extraction resulted when TFN, known to enrich for *T. ferrooxidans*, was added to the On solution. However, the addition of TCN, known to enrich for *T. cuprinus*, resulted in a significant increase in copper extraction ($p = 0.011$) as shown in Table 8.

Microbial seeding of On solution amended with TCN with *T. cuprinus* did not result in substantially more copper extraction than the addition of TCN alone as shown in Table 8. These results suggest that managing dump leach solutions in such a manner as to enhance the activity of the native microorganisms will result in increased copper extraction and that seeding of On solution is not necessary.

Figure 2:
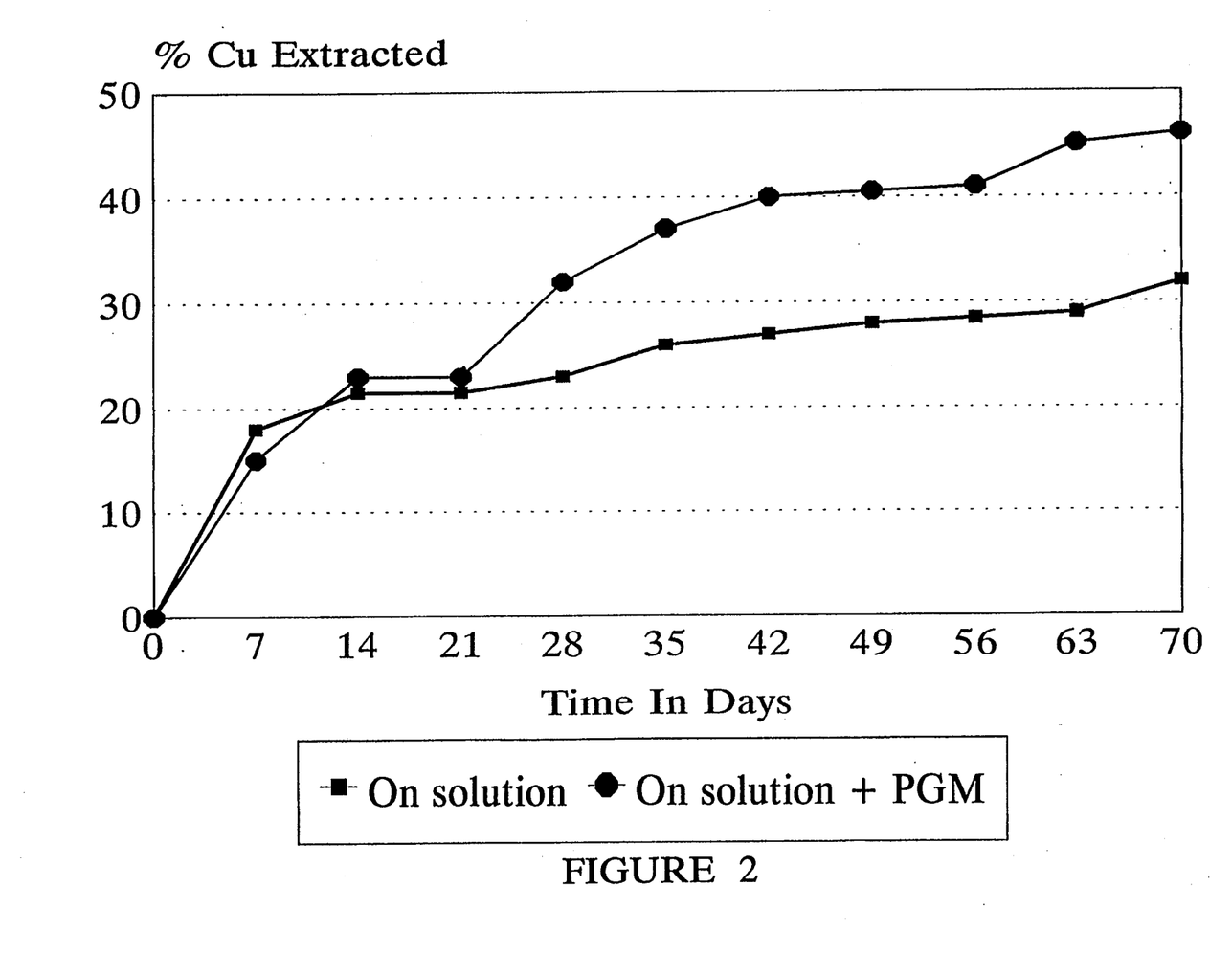
FIG. 2. Rates of copper extraction from sulfide ore by unmodified On solution and On solution amended with PEGM.

This conclusion was further supported by the results obtained when PEGM was added to the On solution. As shown in Table 8, the addition of PEGM resulted in a very significant increase in copper extraction compared to using the unmodified On solution ($p = 0.002$). The effect of PEGM was most noticeable late in the study (see FIG. 2). Copper extraction results were equivalent through Day 21 and both curves appeared to have had "flattened out." However, by Day 28, the beneficial effect of PEGM began to make itself evident. By Day 70, when the study was terminated, the enhancement of copper extraction by the addition of PEGM was marked.

Figure 3:
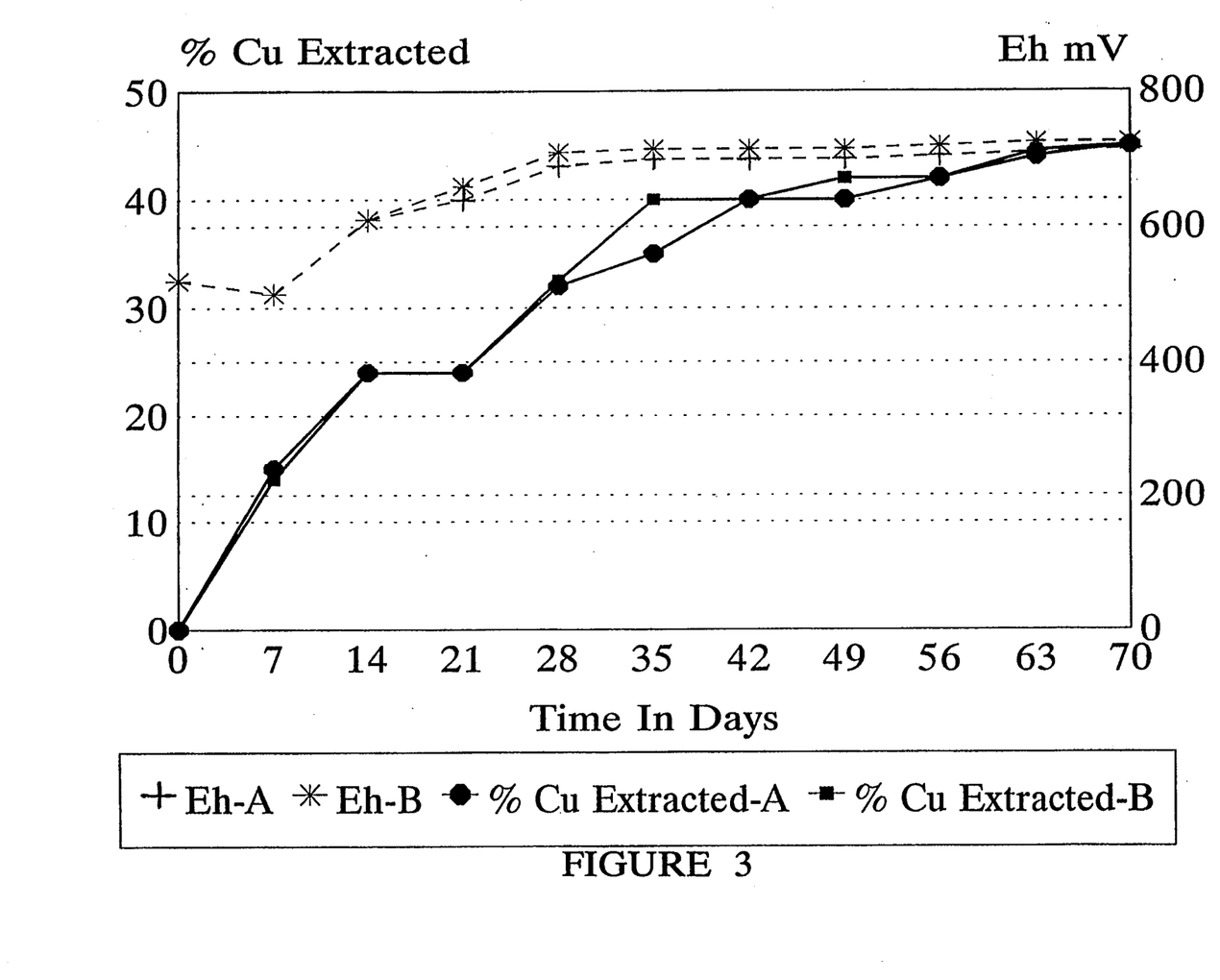
FIG. 3. Rates of copper extraction and eh values from duplicate shake flask tests using low grade sulfide ore and On solution plus PEGM.
Figure 4:
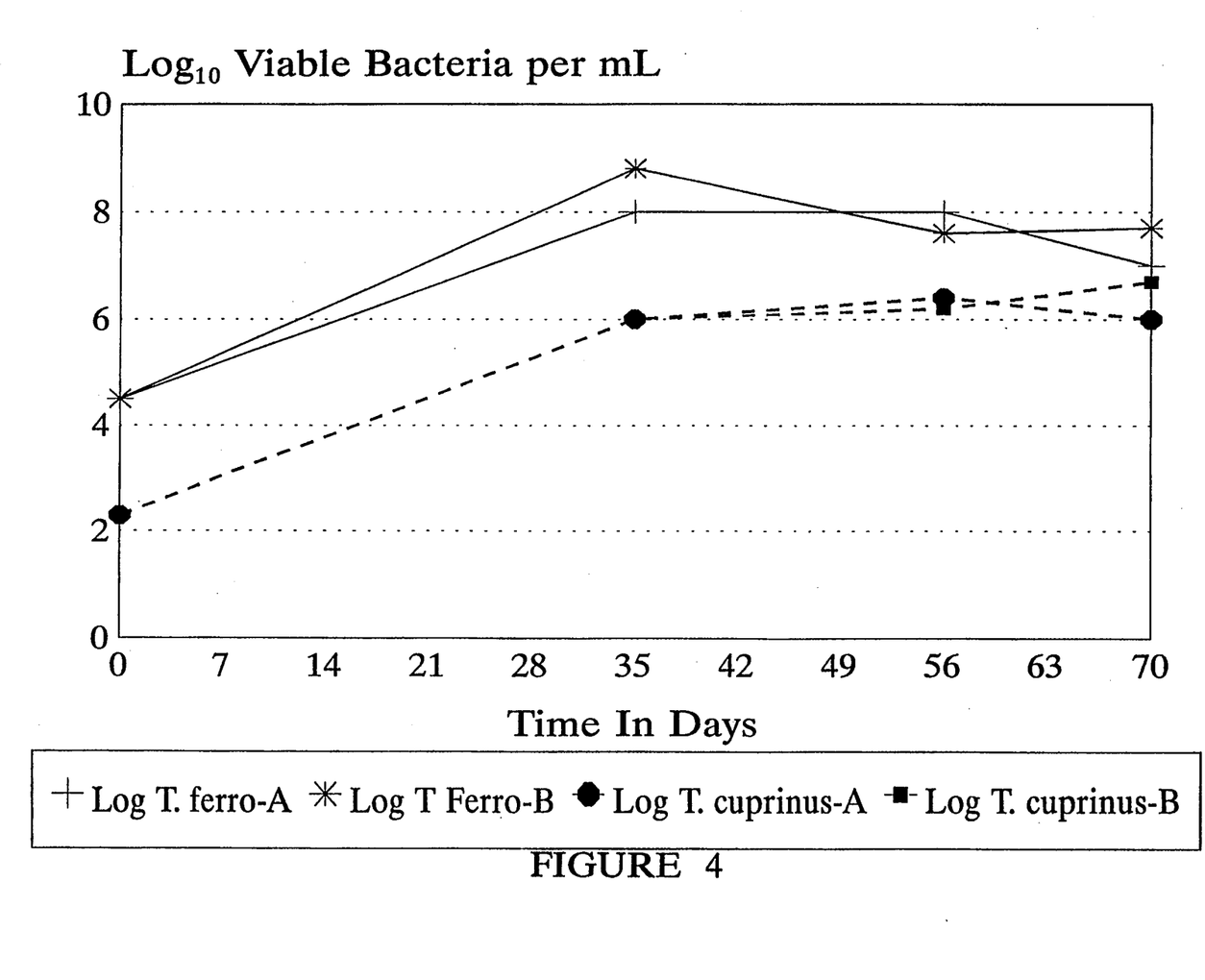
FIG. 4. Population densities of *T. ferrooxidans* (*T. ferro.*) and *T. cuprinus* in leach solutions from duplicate shake flask tests using a low grade copper sulfide ore and On solution plus PEGM.

The effects of PEGM additions were very reproducible. The rates of copper extraction and Eh values in the duplicate shake flask tests are shown in FIG. 3. Except for an early temporary decrease, the Eh values remained high throughout the test. The ability of PEGM-amended On solutions to support populations of *T. ferrooxidans* and *T. cuprinus* was also very reproducible as shown in FIG. 4. Although these bacterial populations were initially low, they both exhibited a 4 log increase in numbers during the shake flask study. The numbers of native *T. ferrooxidans* were consistently 1 log lower in unmodified On solution than in On solution amended with PEGM. Although the PEGM nutrient contains an organic fraction, it surprisingly and advantageously enhanced the growth of *T. ferrooxidans* in the On solution.

In testing the effects of additives to the On Solution in concentrations equivalent to those of growth media, slightly more copper was extracted in the presence of Medium 64, however, the differences in extraction using Medium 64, Medium 64 without ferrous sulfate, (Medium 64-), or Medium 30 were not significant. Medium 64 enriches for iron-oxidizing bacteria such as *T. ferroxidans* and *L. ferrooxidans* while Medium 30 enriches for *T. cuprinus* and similar bacteria. Unlike *T. ferrooxidans*, *T. cuprinus* is able to use many forms of organic carbon including yeast extract as described by Huber and Stetter (1986, 1990). *Thiobacillus cuprinus* prefers a higher pH range (2.5–7.2) than *T. ferrooxidans* (1.3–4.5). *Thiobacillus cuprinus* is also dissimilar to *T. ferrooxidans* in that it is able to oxidize sulfides but not ferrous iron. In spite of this, the solution Eh results using Medium 64 and Medium 30 were similar with average values of 559 and 570 respectively.

In order to directly compare copper extraction by *T. ferrooxidans* and *T. cuprinus*, the ore was sterilized by autoclave prior to seeding Medium 64- and Medium 30 with pure log phase culture of *T. ferrooxidans* and *T. cuprinus* respectively.

Figure 5:
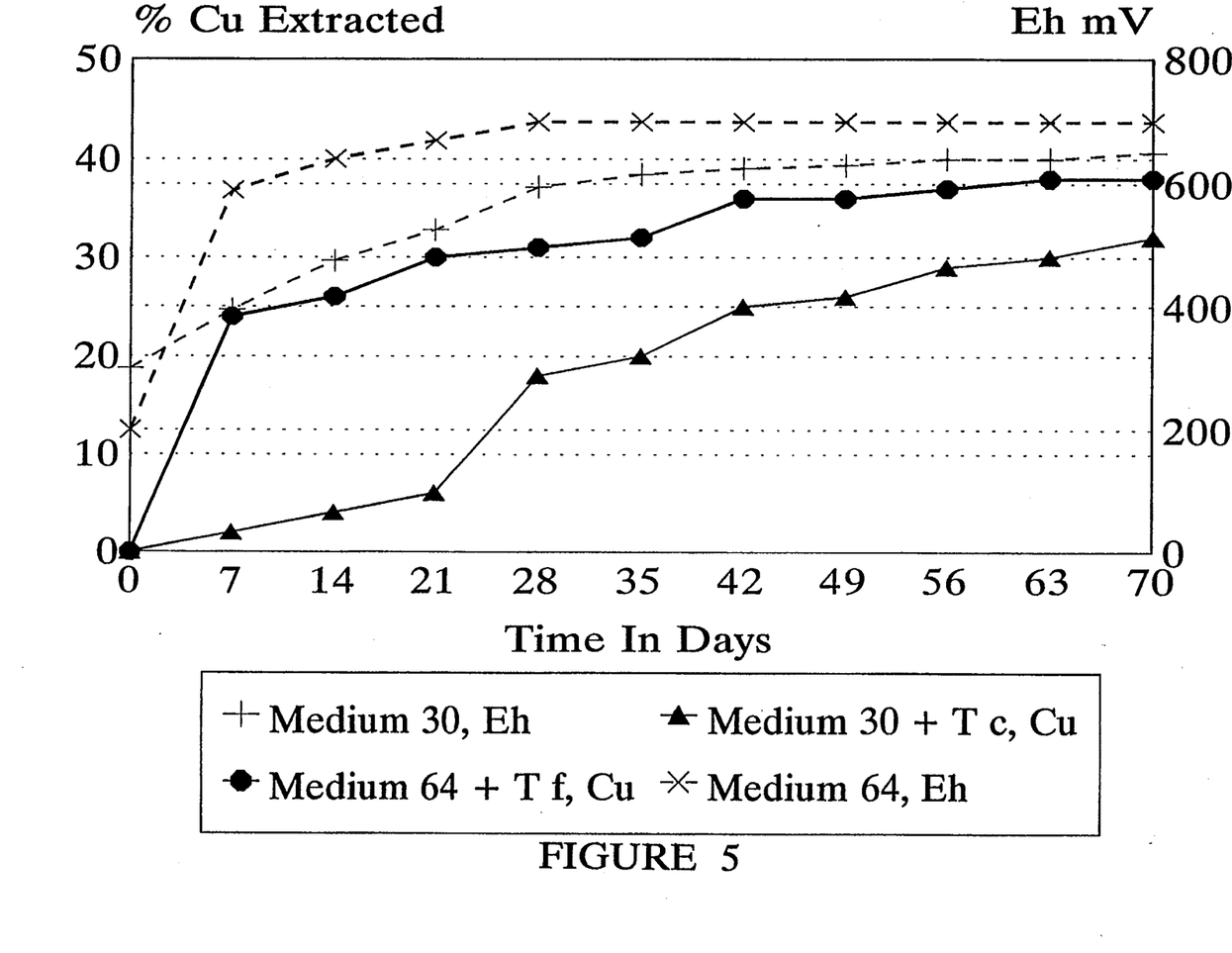
FIG. 5. Rates of copper extraction from sulfide ore using pure bacterial cultures in growth media. T.c. = T. cuprinus, T.f. = T. ferrooxidans.

Significantly more copper was extracted using Medium 64- seeded with *T. ferrooxidans* than by using Medium 30 seeded with *T. cuprinus* (Table 8). In this case, where the ore microcosm was eliminated, Eh values and rates of copper extraction were not equivalent in the two systems as shown in FIG. 5. These results indicated that *T. ferrooxidans* extracted copper more rapidly from sulfide ore A than *T. cuprinus* when competition and cooperation from native ore flora had been eliminated.

EXAMPLE 2

Effect of PEGM Enhancement on the Extraction of Copper from Sample Ore B

Similar enhancement of copper extraction by the addition of PEGM to On solution has also been demonstrated using another sulfide dump ore (Ore Sample B). The primary copper mineral in this ore was chalcopyrite. Metallurgical balances are shown in Table 9. The increased copper extraction achieved by the addition of PEGM was significant (p=0.043).

TABLE 9

| Leach Solution | Metallurgical Balances for Ore Sample B[1] | | | |
|---|---|---|---|---|
| | Cu in Solution | Cu in Leached Tails | Calc. Head | % Cu Extr. |
| On Soln. | 5.3 | 13.3 | 18.6 | 28.5 |
| On Soln. + PEGM | 9.1 | 9.8 | 18.8 | 48.1 |

We also found that the addition of TCN to the On solution and seeding with T. cuprinus enhanced copper extraction much more than the addition of TFN and seeding with T. ferrooxidans during shake flask tests utilizing Ore Sample B. Indeed, 64% of the copper was extracted using nutrient-amended On solution seeded with T. cuprinus. Equivalent concentrations of copper (42%) were extracted from the sulfide ore sample using T. ferrooxidans and T. cuprinus in appropriate laboratory growth media. These results have been described in detail by Rusin et al. (1993).

The addition of TCN and seeding with T. cuprinus can be beneficial for the extraction of copper from sulfide dump ores. However, the bacterial seeding may be unnecessary and the yeast extract present in TCN would not be commercially affordable. The addition of PEGM to On solution showed very reproducible results, growth enhancement of T. ferrooxidans, and significant increases in extraction of copper from two different sulfide dump ores.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

APHA, AWWA, WPCF (1989) "Estimation of Bacterial Density," *Standard Methods for the Examination of Water and Wastewater*, eds. L. S. Cleseri, A. E. Greenberg, and R. R. Trussell, 17ed., pp. 9.77–9.79.

ATCC Catalogue of Bacteria & Bacteriophages (1989) 17th ed., P. 293.

Balch, W. E., G. E. Fox, L. J. Magrum C. R. Woese, and R. S. Wolfe (1979) "Methanogens: Reevaluation of a Unique Biological Group," *Microbiological Reviews* 43:260–296.

Colmer, A. R., and M. E. Hinkle (1947) *Science* 106:253–256.

Gibbs, C. R. (1976) "Characterization and Application of FerroZine Iron Reagent as a Ferrous Indicator, *Analytical Chemistry* 48:1197–1201.

Huber, G., H. Huber, and K. O. Stetter (1986) "Isolation and Characterization of New Metal-Mobilizing Bacteria," *Biotechnology and Bioengineering* 16:239–251.

Huber, H., and K. O. Stetter (1989) "*Thiobacillus prosperus* sp. nov., Represents a new Group of Halotolerant Metal-Mobilizing Bacteria Isolated from a Marine Geothermal Field,"0 *Archives of Microbiology* 151:479–485.

Huber, G., and K. O. Stetter (1990) "*Thiobacillus cuprinus* sp.; a Novel Facultatively Organotrophic Metal-Mobilizing Bacterium," *Applied and Environmental Microbiology* 56:315–322.

Manchee, R. (1979) "*Microbial mining*," TIBS April: 77–80.

Puhakka, J. P., and O. H. Tuovinen (1987) "Effect of Organic Compounds on the Microbiological Leaching of a Complex Sulphide Ore Material" MIRCEN *Journal of Applied Microbiology and Biotechnology* 3:436–442.

Rusin, P. A., L. Quintana, and J. Cassells (1993) "Enhancement of Copper and Molybdenum Bioextraction from Sulfide Ore through Nutrient Balance and the Addition of *Thiobacillus cuprinus*" *Minerals Engineering* 6:977–989.

Stevens, C. J., P. R. Dugan, and O. H. Tuovinen (1986) "Acetylene Reduction (Nitrogen Fixation) by *Thiobacillus ferrooxidans*" *Biotechnology and Applied Biochemistry* 8:351–359.

Torma, A. E., G. G. Gabra, R. Guay, and M. Silver (1976) "Effects of Surface Active Agents on the Oxidation of Chalcopyrite by *Thiobacillus ferrooxidans*," *Hydrometallurgy* 1:301–309.

Tuovinen, O. H., F. A. Panda, and H. M. Tsuchiya (1979) "Nitrogen Requirement of Iron-Oxidizing Thiobacilli for Acidic Ferric Sulfate Regeneration," *Applied and Environmental Microbiology* 37:954–958.

Tuttle, J. H., and P. R. Dugan (1976) "Inhibition of Growth, Iron, and Sulfur Oxidation in *Thiobacillus ferroxidans* by Simple Organic Compounds," *Canadian Journal of Microbiology* 22:719–730.

Rusin, Patricia A. and James E. Sharp (1993) U.S. Pat. No. 5,248,329.

We claim:

1. A process for recovering heavy metals from sulfide ore having indigenous microorganisms comprising the steps of (a) contacting said ore in the presence of oxygen, with an aqueous nutrient supplement comprising carbohydrates and proteins wherein there is more carbohydrate than protein, and wherein said supplement, when applied to said sulfide ore, supports the growth of said indigenous microorganisms, (b) incubating said ore with said supplement for a period of time sufficient to solubilize said heavy metals, (c) collecting said solubilized ore, and (d) treating said solubilized ore to extract said heavy metals.

2. The process, according to claim 1, wherein said nutrient supplement comprises protein, carbohydrates, sulfur, niacin, thiamine, riboflavin, phosphorous and magnesium.

3. The process, according to claim 1, wherein said nutrient supplement is selected from the groups consisting of potato extract growth medium and corn extract growth medium.

4. The process, according to claim 1, wherein said nutrient supplement is potato extract growth medium comprising:

| Ingredient | Concentration Range (%) |
|---|---|
| Protein | 2.0–3.0 |
| Carbohydrate | 18–22 |
| Niacin | 0.0012–0.0010 |
| Thiamine | 0.00005–0.00003 |
| Riboflavin | 0.00002–0.00006 |
| Phosphorous | 0.02–0.08 |
| Potassium | 0.2–0.6 |
| Magnesium | 0.02–0.04 |
| Sulfur | 0.01–0.03. |

5. The process, according to claim 1, wherein said potato extract growth medium comprises:

| Ingredient | Approximate Concentration (%) |
|---|---|
| Protein | 2.5 |

-continued

| Ingredient | Approximate Concentration (%) |
|---|---|
| Carbohydrate | 20.3 |
| Niacin | 0.0015 |
| Thiamine | 0.0001 |
| Riboflavin | 0.00004 |
| Phosphorous | 0.05 |
| Potassium | 0.41 |
| Magnesium | 0.03 |
| Sulfur | 0.02. |

6. The process, according to claim 1, wherein said nutrient supplement is potato extract growth medium having the following composition:

| Ingredient | Concentration Range % |
|---|---|
| Water | 69–85 |
| Ash | 0.08–1.2 |
| Protein | 2.0–3.0 |
| Fat | 0.08–0.13 |
| Fiber | 0.2–0.6 |
| Carbohydrate | 18–22 |
| Total Carbon | 8–10 |
| Starch | 16–20 |
| Glucose | 0.4–0.6 |
| Vitamin A | trace |
| Ascorbic Acid | 0.01–0.03 |
| Niacin | 0.0012–0.0018 |
| Thiamine | 0.00005–0.0003 |
| Riboflavin | 0.00002–0.00006 |
| Iron | 0.01–0.0005 |
| Phosphorus | 0.02–0.08 |
| Potassium | 0.2–0.6 |
| Sodium | 0.01–0.03 |
| Chlorine | 0.05–0.1 |
| Copper | 0.0002–0.0006 |
| Magnesium | 0.02–0.04 |
| Manganese | 0.0007–0.002 |
| Calcium | 0.05–0.02 |
| Sulfur | 0.01–0.03. |

7. The process, according to claim 1, wherein said potato extract growth medium has the following composition:

| Ingredient | Composition |
|---|---|
| Water | 77 |
| Ash | 1 |
| Protein | 2.5 |
| Fat | 0.1 |
| Fiber | 0.4 |
| Carbohydrate | 20.3 |
| Total Carbon | 9 |
| Starch | 18 |
| Glucose | 0.5 |
| Vitamin A | trace |
| Ascorbic Acid | 200 mg/kg (0.02%) |
| Niacin | 15 mg/kg (0.0015%) |
| Thiamine | 1.0 mg/kg (0.0001%) |
| Riboflavin | 0.4 mg/kg (0.00004%) |
| Iron | 0.001 |
| Phosphorus | 0.05 |
| Potassium | 0.41 |
| Sodium | 0.02 |
| Chlorine | 0.07 |
| Copper | 4.1 mg/kg (0.00041%) |
| Magnesium | 0.03 |
| Manganese | 9.6 mg/kg (0.00096%) |
| Calcium | 0.01 |
| Sulfur | 0.02. |

8. The process, according to claim 1, wherein said nutrient supplement is corn extract growth medium comprising:

| Ingredient | Range of Concentration (%) |
|---|---|
| Protein | 10.9–13.3 |
| Carbohydrate | 76.0–92.8 |
| Niacin | 0.01–0.05 |
| Thiamine | 0.00027–0.00033 |
| Riboflavin | 0.0012–0.0014 |
| Phosphorous | 0.2–0.4 |
| Sulfur | 0.08–0.13 |
| Potassium | 0.2–0.6 |
| Magnesium | 0.116–0.144. |

9. The process, according to claim 1, wherein said corn extract growth medium comprises:

| Ingredient | Approximate Concentration (%) |
|---|---|
| Protein | 12.1 |
| Carbohydrate | 84.4 |
| Niacin | 0.03 |
| Thiamine | 0.0003 |
| Riboflavin | 0.0013 |
| Phosphorous | 0.34 |
| Sulfur | 0.1 |
| Potassium | 0.4 |
| Magnesium | 0.13. |

10. The process, according to claim 1, wherein said nutrient supplement is corn extract growth medium having the following composition:

| Ingredient | Range of Concentration (%) |
|---|---|
| Ash | 1.46–1.74 |
| Fiber | 2.4–3.0 |
| Protein | 10.9–13.3 |
| Fat | 4.9–5.9 |
| Carbohydrate | 76.0–92.8 |
| Vitamin A (IU) | 282–338 |
| Ascorbic acid | 0.01–0.03 |
| Niacin | 0.01–0.05 |
| Thiamine | 0.00027–0.00033 |
| Riboflavin | 0.0012–0.0014 |
| Iron | 0.0009–0.0013 |
| Magnesium | 0.116–0.144 |
| Phosphorous | 0.2–0.4 |
| Sulfur | 0.08–0.13 |
| Potassium | 0.2–0.6 |
| Calcium | 0.01–0.03 |
| Choline | 0.5–0.7 |
| Pantothenic acid | 0.0062–0.0078 |
| Pyridoxine | 0.0079–0.01 |
| Arginine | 0.5–0.7 |
| Cystine | 0.7–0.2 |
| Glycine | 0.4–0.6 |
| Histidine | 0.1–0.3 |
| Isoleucine | 0.45–0.55 |
| Leucine | 1.17–1.43 |
| Lysine | 0.15–0.25 |
| Methionine | 0.1–0.3 |
| Phenylalanine | 0.5–0.7 |
| Threonine | 0.4–0.6 |
| Tryptophan | 0.06–0.22 |
| Valine | 0.46–0.56. |

11. The process, according to claim 1, wherein said corn extract growth medium has the following composition:

| Ingredient | Aproximate Concentration % |
|---|---|
| Ash | 1.6 |
| Fiber | 2.7 |
| Protein | 12.1 |
| Fat | 5.4 |
| Carbohydrate | 84.4 |

-continued

| Ingredient | Aproximate Concentration % |
|---|---|
| Vitamin A | 310.0 (IU) |
| Ascorbic acid | 0.02 |
| Niacin | 0.03 |
| Thiamine | 0.0003 |
| Riboflavin | 0.0013 |
| Iron | 0.001 |
| Magnesium | 0.13 |
| Phosphorous | 0.34 |
| Sulfur | 0.1 |
| Potassium | 0.4 |
| Calcium | 0.02 |
| Choline | 0.6 |

-continued

| Ingredient | Aproximate Concentration % |
|---|---|
| Pantothenic acid | 0.007 |
| Pyridoxine | 0.009 |
| Arginine | 0.6 |
| Cystine | 0.1 |
| Glycine | 0.5 |
| Histidine | 0.2 |
| Isoleucine | 0.5 |
| Leucine | 1.3 |
| Lysine | 0.2 |
| Methionine | 0.2 |
| Phenylalanine | 0.6 |
| Threonine | 0.5 |
| Tryptophan | 0.1 |
| Valine | 0.5. |

* * * * *

UNITED STATES PATENT AND TRADEMARK OFFICE
CERTIFICATE OF CORRECTION

PATENT NO. : 5,413,624
DATED : May 9, 1995
INVENTOR(S) : Patricia A. Rusin and James E. Sharp It is certified that error appears in the above-indentified patent and that said Letters Patent is hereby corrected as shown below:

Column 3, line 41: Delete "ore pries using" and insert --ore piles using--.

Column 3, line 53: Delete "heap pries" and insert --heap piles--.

Column 6, line 43: Delete "0.1% sodium solution" and insert --0.1% sodium benzoate solution--.

Column 6, line 49: Delete "and minus200 mesh" and insert --and minus 200 mesh--.

Column 9, line 10: Insert footnote --[1]Head assay in all cases = 18.2 mg. All values expressed as mg unless designated otherwise--.

Column 9, line 59: Delete "Field,'0 Archives" and insert --Field," Archives--.

Signed and Sealed this

Third Day of October, 1995

Attest:

BRUCE LEHMAN

*Attesting Officer*   *Commissioner of Patents and Trademarks*